United States Patent
Neuß

(10) Patent No.: US 11,819,429 B2
(45) Date of Patent: Nov. 21, 2023

(54) DOUBLE STENT

(71) Applicant: Bentley InnoMed GmbH, Hechingen (DE)

(72) Inventor: Malte Neuß, Bonn (DE)

(73) Assignee: Bentley InnoMed GmbH, Hechingen (DE)

(*) Notice: Subject to any disclaimer, the term of this patent is extended or adjusted under 35 U.S.C. 154(b) by 0 days.

(21) Appl. No.: 16/979,835

(22) PCT Filed: Mar. 14, 2019

(86) PCT No.: PCT/EP2019/056453
§ 371 (c)(1),
(2) Date: Sep. 10, 2020

(87) PCT Pub. No.: WO2019/175330
PCT Pub. Date: Sep. 19, 2019

(65) Prior Publication Data
US 2021/0052402 A1    Feb. 25, 2021

(30) Foreign Application Priority Data
Mar. 14, 2018 (DE) .................. 10 2018 105 925.6

(51) Int. Cl.
*A61F 2/852* (2013.01)
*A61F 2/915* (2013.01)
(Continued)

(52) U.S. Cl.
CPC .............. *A61F 2/852* (2013.01); *A61F 2/07* (2013.01); *A61F 2/915* (2013.01); *A61F 2/856* (2013.01);
(Continued)

(58) Field of Classification Search
CPC ......... A61F 2/06–2002/077; A61F 2250/0048; A61F 2250/0031; A61F 2210/0076
See application file for complete search history.

(56) References Cited

U.S. PATENT DOCUMENTS

| | | | |
|---|---|---|---|
| 2005/0203606 A1* | 9/2005 | VanCamp | A61F 2/82 623/1.15 |
| 2008/0262593 A1* | 10/2008 | Ryan | A61F 2/852 623/1.12 |

(Continued)

FOREIGN PATENT DOCUMENTS

| | | |
|---|---|---|
| DE | 19720115 A1 | 12/1998 |
| DE | 29623983 U1 | 1/2001 |

(Continued)

OTHER PUBLICATIONS

Machine translation of WO2017125312A1, 5 pages, accessed Sep. 23, 2021 (Year: 2021).*

(Continued)

*Primary Examiner* — Rebecca S Preston
(74) *Attorney, Agent, or Firm* — Brooks Kushman P.C.

(57) ABSTRACT

The invention relates to a double stent comprising two coaxially arranged stents (2, 3), wherein a first membrane (4) being arranged between a first inner stent (2) and the second outer stents (3), and a second membrane (5) being arranged on the second stent (3), with the membrane ends of the first and second membrane (4, 5) being brought together at the ends of the stents (2, 3) and folded over onto the inside of the first stent (2) and secured/fixed there.

14 Claims, 2 Drawing Sheets

Figure 1:
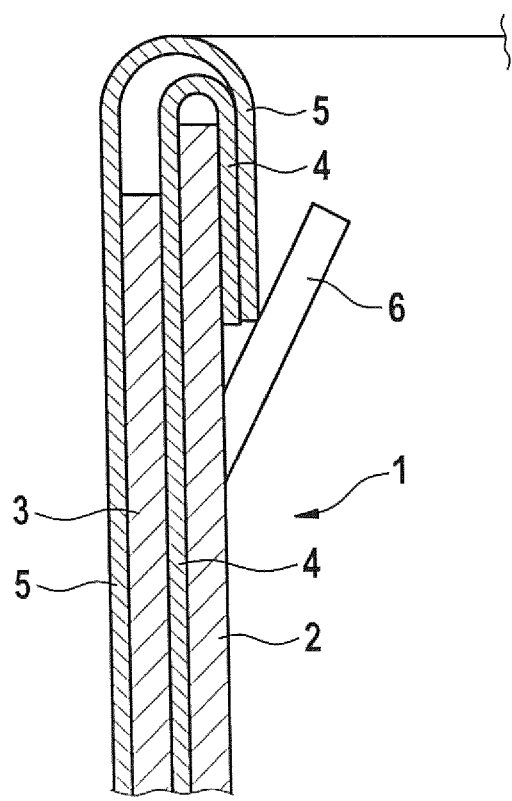

(51) Int. Cl.
*A61F 2/07* (2013.01)
*A61F 2/856* (2013.01)

(52) U.S. Cl.
CPC ............... *A61F 2002/91516* (2013.01); *A61F 2002/91575* (2013.01); *A61F 2210/0004* (2013.01); *A61F 2210/0014* (2013.01); *A61F 2210/0076* (2013.01); *A61F 2220/0016* (2013.01); *A61F 2220/0025* (2013.01); *A61F 2250/0031* (2013.01); *A61F 2250/0037* (2013.01); *A61F 2250/0039* (2013.01); *A61F 2250/0048* (2013.01); *A61F 2250/0069* (2013.01)

(56) References Cited

U.S. PATENT DOCUMENTS

| | | | |
|---|---|---|---|
| 2009/0005857 A1* | 1/2009 | Ischinger | A61F 2/82 623/1.18 |
| 2009/0043330 A1* | 2/2009 | To | A61F 2/07 606/194 |

FOREIGN PATENT DOCUMENTS

| | | | | |
|---|---|---|---|---|
| DE | 102015106052 A1 | 10/2016 | | |
| EP | 3563809 A1 * | 11/2019 | ............... | A61F 2/86 |
| RU | 2566225 C2 | 10/2015 | | |
| WO | WO2012/084202 A2 | 6/2012 | | |
| WO | WO2017/125312 A1 | 7/2017 | | |
| WO | WO2017125312 A | 7/2017 | | |
| WO | WO2018078019 A | 5/2018 | | |

OTHER PUBLICATIONS

Russian Office Action dated Nov. 30, 2021 in connection with related Russian Patent Application No. 2020132488.

Indian Office Action dated Jul. 6, 2022 in connection with related Indian Patent Application No. 202047039823.

* cited by examiner

ERSATZBLATT (REGEL 26)

DOUBLE STENT

The invention relates to a double stent comprising two coaxially arranged stents, wherein a first membrane is arranged between a first inner stent and a second outer stent and a second membrane is arranged on the second stent and wherein the membrane ends of the first and second membrane are brought together at the ends of the stent and are folded over onto the inside of the first stent where they are clamped in place.

The double stent is used in particular as a stent graft for the purpose of bridging vascular malformations, such as aneurysms and shunts, but also to reinforce unstable, fragile or thrombotic vessel walls. It is, moreover, applied as a bridging element for branches out of stented vessels or prostheses.

Stent grafts for bridging vascular malformations are known in a variety of forms. As a rule, they consist of a stent that is completely or partially covered with a membrane. The membrane occludes the vascular malformation against the vessel, the stent keeps the vessel open and ensures that the membrane is in close contact with the vessel wall.

A problem encountered with stent grafts involves anchoring the membrane to the stent. For this purpose, double stents were developed in which the membrane is kept in place between an outer and an inner stent. During the expansion of such a double stent, the membrane participates in the radial expansion but remains clamped between the two stents.

Such a double stent is known, for example, from what has been disclosed in DE 197 20 115 A1. The stent described in that publication has proven its worth in and of itself, but can be improved in two respects.

On the one hand, problems with tightness are often faced, as the membrane is not in close contact with the vessel wall and/or is damaged during the expansion of the double stent. In both cases, the double stent does not meet the requirements placed on it, namely the occlusion of, for example, a vascular malformation.

On the other hand, the expansion of the double stent may cause the composite of two stents and a membrane to lose coherence, for example if the two stents exhibit a different expansion behavior—for example due to local conditions.

Double stents that consist of a combination of two balloon-expandable stents usually exert a high radial force, which leads to a reliable placement and fixation of the membranes. However, the high radial force is associated with a loss of flexibility. In addition, considerable pressures are required for the expansion process. The wall thickness of such a double stent equipped with membranes should be kept within limits in order not to unnecessarily narrow the vessel volume, but without compromising on functionality.

It is, therefore, the objective of the present invention to provide a double stent that meets the requirements with respect to tightness and reliability, ensures the necessary coherence, and exerts a sufficiently high radial force. Moreover, the stent should have sufficient flexibility.

This objective is achieved with a double stent of the kind first mentioned above, in which the two stents are made of different materials.

In the double stent proposed by the present invention, the inner and outer stent differ both with respect to properties and materials used. One of the stents is a balloon-expandable stent that provides the required radial force, while the other stent is made of another material having a lower radial force, such as a biodegradable material, or being a shape memory alloy that has self-expanding characteristics. Materials of this kind are known and have frequently been described in literature. The stent with the lower radial force is more flexible, that is, its wall thickness can be kept smaller. In particular, it serves for the fixation of the first and/or second membrane.

The balloon-expandable stent exerting high radial force is especially a stent consisting of a cobalt-chromium alloy as it is conventionally used as a vessel supporting device. Such a balloon-expandable stent may be used both internally and externally facing the vessel wall, that is to say, may serve as a first inner or second outer stent. If it is used as first inner stent, it also serves to secure the ends of the membrane. In the event it is applied as a second outer stent, it provides the necessary contact pressure, which on the one hand serves to secure the double stent to the vessel wall, where necessary also to expand the vessel, but also to anchor the outer membranes to the vessel wall.

The other stent exerting lower radial force may, for example, be a biodegradable stent, as it is commonly manufactured of biodegradable plastics (polylactides and/or polygalactides) and often described in literature. Biodegradable metal stents, for example those made of magnesium alloys, are also suitable for this purpose and have also been frequently referred to in detail in literature. Such a stent can exclusively be used as a second outer stent and serves for the fixation of the outer membranes to the vessel wall and the inner membrane in the composite stenting system.

Alternatively, the stent exhibiting the lower radial force may be made of a nickel-titanium alloy, such as Nitinol. Such a stent may be employed as the first inner stent as well as the second outer stent. When used as first inner stent, it makes sure the ends of the membrane are secured and produces the necessary contact pressure for the inner membranes to the second outer stent. When serving as second outer stent, it ensures rapid fixation of the outer membranes to the vessel wall during the expansion phase and that the inner membrane is properly seated between the two stents of the composite stenting arrangement.

The combination of a stent consisting of a cobalt-chromium alloy with a self-expanding stent made of a nickel-titanium alloy is preferred, with the latter stent being particularly preferred as the first inner stent of the composite double stenting system.

In this case, it is considered expedient and appropriate for the first inner stent to be 5 to 10 mm, preferably 8 mm, longer than the second outer stent and, in its final form as determined by its shape memory characteristics, to have a diameter 1 to 6 mm, preferably 3 mm, larger than that of the second outer stent. Due to this oversize in diameter it is ensured that in the final state the inner membrane will always remain sufficiently tightly clamped between the inner stent and the outer stent.

For better anchoring of the double stent in a vessel or prosthesis, the first inner stent may additionally be fitted with radially protruding barbs or have a trumpet-shaped formation, which can be coated with ePTFE if required.

The double stent proposed by the invention not only comprises an inner and an outer stent but is also provided with an inner and outer membrane. Here, the two membranes complement each other in terms of impermeability. The outer second membrane serves as protection and supplement to the inner first membrane so that, if the inner membrane is damaged during expansion, for example tears, the outer membrane is capable of compensating for this defect and vice versa. Furthermore, the outer membrane holds the construct together, whereby anchoring the ends of the outer membrane—together with the ends of the inner membrane—on the inside of the inner stent contributes to the coherence of the elements.

For the stents used according to the invention, the usual stent designs can be put to use, such as those often developed for balloon-expandable and self-expanding stents. For balloon-expandable stents any materials customary for this purpose may be employed, for example, steel alloys appropriate for medical use, cobalt-chromium alloys and the like. As regards self-expanding stents, materials with shape memory properties are particularly suitable, such as nickel-titanium alloys.

The stents are usually cut from a tube of suitable diameter using a laser cutting technique. They have a mesh structure with ring segments and connecting webs between the ring segments.

For example, the stents may have a mesh structure as formed by intersecting webs. Stents consisting of a plurality of meandering ring segments are preferred, with said ring segments being connected to adjacent ring segments by means of connecting webs. In this case, too, meshes are produced, the size of which is determined by the frequency of the connecting webs existing between two adjacent ring segments. Such a stent structure is suited to at least partially compensate for the length reduction that occurs during expansion depending on the arrangement and shape of the connecting webs.

Various methods can be adopted to secure the membranes to the inside of the inner stent. On the one hand the membranes can be sewn or glued. Welding, for example by ultrasonic method, or fusing, even through the meshes of the inner stent, is preferred when the stent is subjected to initial dilatation during manufacture. Subsequently, the completed double stent is crimped onto a balloon.

The membranes on the first inner stent may also be clamped in place, for example, to flexible tongues existing there. The flexible tongues point into a direction outwards of the stent, i.e. they point to the edge of the stent. Such flexible tongues can, for example, be outward facing membrane arches of the ring segments, with the foil ends being clamped in place between the membrane arches and the connecting webs originating from the same ring segment (WO 2012/084202 A2). Clamping the membrane ends on the inside of the inner stent results in reliably anchoring and securing the two membranes and strengthens the composite comprising the inner stent, the inner membrane, the outer stent and the outer membrane.

Any biological or artificial material suitable for the purpose can be employed for the membranes. Usually, the membranes consist of plastic material, preferably a plastic tube, which is pulled over the respective stent. For example, a suitable material is polytetrafluoroethylene, PTFE, especially ePTFE, which has the elasticity required for the expansion process. Other plastics unobjectionable from a medical viewpoint, such as polyester, polyolefins, polyurethanes, polyurethane carbonate and the like, may also be employed.

It goes without saying that different designs can be used for the inner and outer stent, and the inner and outer membrane can be produced of different materials.

The application of two stents and two membranes naturally leads to a relatively high wall thickness of the construct, which limits maneuverability in a patient's vascular system. This can be counteracted by selecting a low wall thickness of the tubes from which the stents are cut, especially for the stent having a lower radial force, for example in the range of between 0.05 and 0.50 mm, preferably between 0.10 and 0.20 mm and in particular approx. 0.15 mm. The web width as well can be reduced, for example, to between 0.05 and 0.50 mm, preferably between 0.10 and 0.20 mm and in particular approx. 0.15 mm.

It is preferred, moreover, to provide the outer stent with meshes that are smaller than those of the inner stent. In this way, a compressive stress is created during expansion, which has an advantageous effect on the radial force and the coherence of the construct. This ensures that high strength and durability of the construct are achieved.

The inventive double stent is particularly suitable for placement in branches of stented vessels and thus for bridging the space that forms between the stented vessel and the branch.

Figure 2:
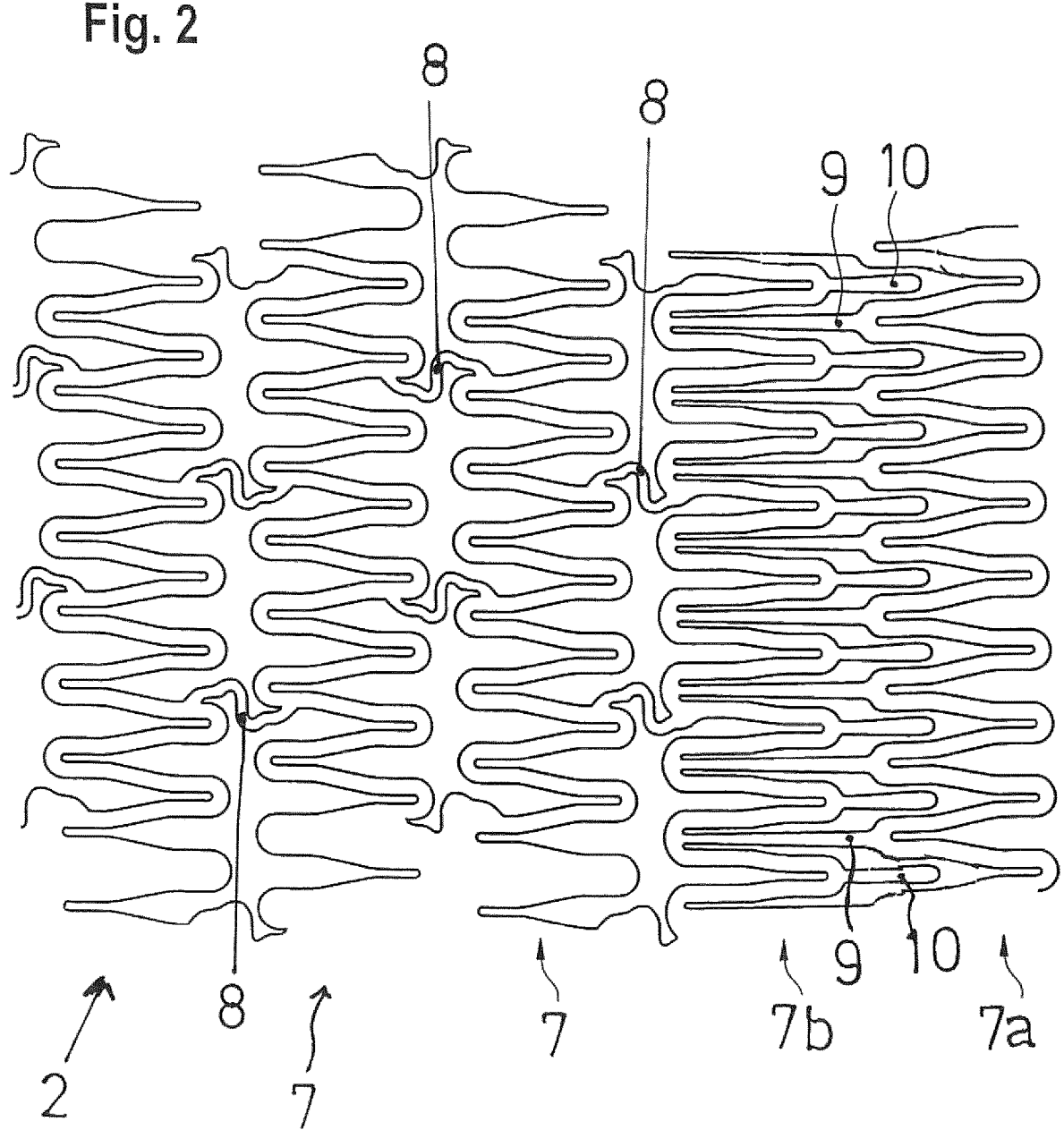
Figure 3:
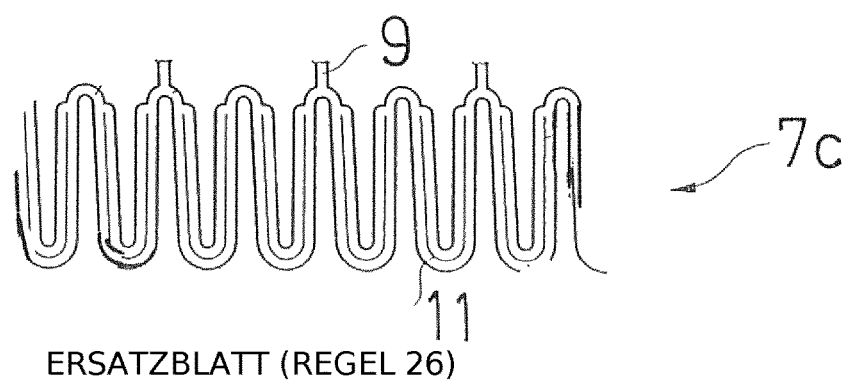

Further elucidation of the invention is provided through the enclosed figures showing preferred embodiments of the invention. It goes without saying that the characteristics shown in the figures shall in each case be regarded individually as being part of the invention and should not be understood exclusively in the context of the other characteristics illustrated in the figures, where FIG. 1: illustrates schematically a longitudinal section through the end area of the wall of a double stent according to the invention;

FIG. 2: shows a top view of the developed wall of the inner stent in the area of its end section;

FIG. 3: shows a variant with respect to FIG. 2.

The double stent proposed by the invention and designated in FIG. 1 as a whole with the reference numeral 1 comprises a first inner stent 2 and a second outer stent 3 which are arranged coaxially to each other. The outer stent 3 is slightly shorter than the inner stent 2. The entire double stent 1 is shown in the non-expanded state. Between the inner stent 2 and the outer stent 3 a first inner membrane 4 is provided. The outer stent 3 is surrounded by a second outer membrane 5. Both membranes 4 and 5 are made of ePTFE.

The inner membrane 4 and the outer membrane 5 are brought together at their ends and folded inwardly into the hollow space of the inner stent 2 around the upper edge of the double stent 1. Shown as an example is one of several flexible tongues 6 forming part of the inner stent 2, said tongues being bent inwards and serving to clamp in place the inwardly folded edges of the membranes 4 and 5.

The inner stent 2, as illustrated in FIG. 1, is expediently manufactured of a suitable shape memory alloy, for example of nickel-titanium (Nitinol), and has proximally an excess length of 5 mm to 10 mm, preferably 8 mm. Moreover, in its final state which is determined by its shape memory characteristics, it has a diameter that is 1 to 6 mm, preferably 3 mm larger than the diameter of the outer stent 3. This ensures that the inner membrane 4 always remains sufficiently tightly clamped between the inner stent 2 and the outer stent 3. For better anchoring in a vessel or prosthesis, the stent 2 may additionally be fitted with radially protruding barbs or have a trumpet-shaped formation, which can be coated with ePTFE if required.

In FIG. 2 the design of the wall of the inner stent 2 has been illustrated in its end area, which is also shown in FIG. 1, but in this case depicting a specific design of the flexible tongues 6, which are only shown schematically in FIG. 1.

As can be seen from FIG. 2, the wall of the inner stent 2 in the longitudinal region of the stent 2 consists of a plurality of ring segments 7, each of which has a circumferential, meandering band.

These meandering bands are axially connected to each other by connecting webs that are resilient in the axial direction. In this respect, the wall structure of the inner stent 2 corresponds to the widely adopted common way of constructing stents.

In contrast to the customary stents, the stent 2 depicted in FIG. 2 has two differently designed ring segments 7a and 7b in the end area, which have been provided with a view to forming out the flexible tongues of the first inner stent 2, which are designated with the reference numeral 6 in FIG. 1 above. In this case, the ring segment 7a forms the final outer edge of the stent 2, while the ring segment 7b is located between the outer edge and the longitudinal area of the stent 2, refer to DE 10 2015 106 052 A1.

Each of the two ring segments 7a and 7b exhibit as well a circumferential, meandering band. The meandering arches of both ring segments 7a and 7b pointing towards the longitudinal area of the stent 2 are connected to each other by axially extending connecting webs 9. In contrast, the meandering arches of the two ring segments 7a and 7b pointing towards the end of stent 2 are not connected to each other. Instead, the meandering arches of ring element 7b pointing towards the end of stent 2 are provided with blind webs 10, which protrude into the meandering arches of ring segment 7a oriented in the same direction, without being connected to them. These blind webs 10, in conjunction with the meandering arches of the ring segment 7b carrying them, form the flexible tongues which are only shown schematically in FIG. 1 and are designated there with the reference numeral 6.

FIG. 3 shows another possible way of forming the flexible tongues referred to hereinbefore, which are marked with the reference numeral 6 in FIG. 1. For this purpose, a ring segment 7c is provided at the end of the inner stent 2, which also has a circumferential, meandering band, the meandering arches of which pointing towards the end of the stent 2 are provided with incisions 11 over their length and thus form elastically deformable flexible tongues capable of clamping between them—like paper clips—the ends of membranes 4 and 5 shown in FIG. 1, refer to WO 2012/084202 A2.

The invention claimed is:

1. Double stent comprising two coaxially arranged stents (2, 3), wherein a first membrane (4) is arranged between a first inner stent (2) and a second outer stent (3) and a second membrane (5) is arranged on the second outer stent (3), wherein membrane ends of the first and the second membranes (4, 5) are brought together at ends of the stents (2, 3) and folded over onto an inner side of the first inner stent (2) and secured/fixed there, wherein the first inner stent (2) is made of a first material and the second outer stent (3) is made of a second material characterized in that the second outer stent (3) consists of a cobalt-chromium alloy and the first inner stent (2) consists of a shape-memory alloy, wherein the first inner stent (2) is 5 to 10 mm longer than the second outer stent (3) and, in its final form as determined by its shape memory characteristics, has a diameter 1 to 6 mm larger than a diameter of the second outer stent (3).

2. Double stent according to claim 1, characterized in that the first inner stent (2) is provided at its proximal end with additional fixation elements.

3. Double stent according to claim 2, characterized in that the additional fixation elements are in the form of barbs and/or a trumpet-shaped widening.

4. Double stent according to claim 1, characterized in that at least the first inner stent (2) is provided with a plurality of ring segments (7, 7a, 7b) arranged side by side and having a meandering structure, said ring segments being connected to one another by means of connecting webs (8, 9).

5. Double stent according to claim 4, characterized in that the connecting webs (8) of the first inner stent (2) and second outer stent (3) are arranged with gaps between them.

6. Double stent according to claim 1, characterized in that the membranes (4, 5) are secured/fixed by gluing/bonding, sewing, welding or clamping.

7. Double stent according to claim 1, characterized in that the membranes (4, 5) are clamped in place in or between flexible tongues (6) formed by applying incisions in meandering arches of the first inner stent (2).

8. Double stent according to claim 7, characterized in that the flexible tongues (6) point outside of the first inner stent.

9. Double stent according to claim 7, characterized in that the flexible tongues (6) are arranged in peripheral regions of the first inner stent (2).

10. Double stent according to claim 9, characterized in that the flexible tongues (6) are formed on ring segments (7b) which are arranged adjacent to peripheral ring segments (7a).

11. Double stent according to claim 1, characterized in that the first membrane (4) and/or second membrane (5) consists of plastic material.

12. Double stent according to claim 11, characterized in that the first membrane (4) and/or the second membrane (5) consists of PTFE.

13. Double stent according to claim 1, characterized in that the first inner stent (2) is 8 mm longer than the second outer stent (3).

14. Double stent according to claim 1, characterized in that the first inner stent (2), in its final form as determined by its shape memory characteristics, has a 3 mm larger diameter than the diameter of the second outer stent (3).

* * * * *